United States Patent
Komoto et al.

(10) Patent No.: US 7,214,672 B2
(45) Date of Patent: May 8, 2007

(54) PREVENTIVES/REMEDIES FOR INFLAMMATORY AIRWAY DISEASES

(75) Inventors: Teruo Komoto, Chiba (JP); Hiroyuki Mizuno, Inba-gun (JP); Yoshinori Takahashi, Inba-gun (JP); Koichi Takahashi, Inba-gun (JP); Susumo Sato, Narita (JP)

(73) Assignee: Nippon Shinyaku Co., Ltd., Kyoto-shi (JP)

(*) Notice: Subject to any disclaimer, the term of this patent is extended or adjusted under 35 U.S.C. 154(b) by 555 days.

(21) Appl. No.: 10/451,061

(22) PCT Filed: Dec. 21, 2001

(86) PCT No.: PCT/JP01/11264

§ 371 (c)(1),
(2), (4) Date: Jun. 20, 2003

(87) PCT Pub. No.: WO02/051422

PCT Pub. Date: Jul. 4, 2002

(65) Prior Publication Data

US 2004/0053904 A1    Mar. 18, 2004

(30) Foreign Application Priority Data

Dec. 22, 2000    (JP) .............................. 2000-390941

(51) Int. Cl.
*A61K 31/56* (2006.01)
*A61K 31/58* (2006.01)

(52) U.S. Cl. .................. 514/178; 514/170; 514/171
(58) Field of Classification Search ........ 514/170–171, 514/178
See application file for complete search history.

(56) References Cited

U.S. PATENT DOCUMENTS

| | | | |
|---|---|---|---|
| 3,639,434 A | 2/1972 | Oxley et al. | |
| 4,024,131 A | 5/1977 | Villax | |
| 4,655,971 A | 4/1987 | Page et al. | |
| 4,933,168 A * | 6/1990 | Jones et al. | 424/45 |
| 5,063,222 A * | 11/1991 | Komoto et al. | 514/180 |

FOREIGN PATENT DOCUMENTS

| EP | 393658 | 10/1990 |
|---|---|---|
| WO | 95/20393 | 8/1995 |

OTHER PUBLICATIONS

Kelly and Hill, "Asthma" in Pharmacotherapy—A Pathophysiologic Approach, 2nd ed., pp. 408-449, 1992, Elsevirt Science Publishing.*
Kelly, The Annals of Pharmacotherapy, 1998;32:220-232.*
J. Med. Chem., vol. 34, No. 8, pp. 2468-2473, 1991.

* cited by examiner

*Primary Examiner*—San-Ming Hui
(74) *Attorney, Agent, or Firm*—Oblon, Spivak, McClelland, Maier & Neustadt, P.C.

(57) ABSTRACT

A preventive and/or therapeutic agent for inflammatory respiratory tract diseases containing, as an active ingredient, a steroid derivative represented by the following formula (1):

n=8 (mean ± standard error)
## : p<0.01 vs physiological saline (unpaired t-test)
** : p<0.01 vs control group (Dunnett's test)

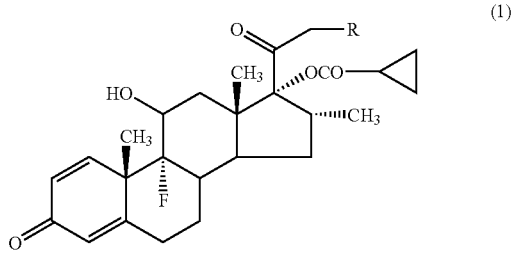

(1)

(wherein R represents a hydrogen atom, a halogen atom, a hydroxy group, or —OCOR$^1$ (wherein R$^1$ represents a linear or branched alkyl group which may be substituted by a halogen atom or a cycloalkyl group; a cycloalkyl group; or an aryl group)).

These compounds can continuously suppress respiratory tract inflammation and respiratory tract hyperreaction and show a high site selectivity and little systemic effect when administered directly to the respiratory tract. By virtue of these characteristics, these compounds are remarkably useful in clinical medicine as highly safe preventive and/or therapeutic agents for inflammatory respiratory tract diseases which can be administered for a long period of time.

6 Claims, 3 Drawing Sheets n = 8 (mean ± standard error)

‡‡ : p<0.01 vs physiological saline (unpaired t-test)

** : p<0.01 vs control group (Dunnett's test)

n = 9 (mean ± standard error)

*, ** : p<0.05 and p<0.01 vs control group (Dunnett's test)

\#; Significant difference against saline group (significance level <5)

\#\#; Significant difference against saline group (significance level <1%)

*; Significant difference against control group (significance level <5%)

**; Significant difference against control group (significance level <1%)

(A)

(B)

; Significant difference against saline group (significance level <1%)

*; Significant difference against control group (significance level <5%)

**; Significant difference against control group (significance level <1%)

PREVENTIVES/REMEDIES FOR INFLAMMATORY AIRWAY DISEASES

TECHNICAL FIELD

The present invention relates to a preventive and/or therapeutic agent for inflammatory respiratory tract diseases such as bronchial asthma and nasal hypersensitivity.

BACKGROUND ART

According to recent studies, respiratory tract diseases including bronchial asthma and nasal hypersensitivity conditions (e.g., allergic rhinitis and vasomotor rhinitis) should be considered to be inflammatory diseases characterized by chronic inflammation of the respiratory tract mucosa in which a variety of phagocytes such as mast cells, eosinophils, and lymphocytes are involved, and also by sthenia in respiratory tract hypersensitivity induced by the inflammation. Thus, therapeutic agents for the respiratory tract diseases have gradually shifted from those containing bronchodilators, antiallergic agents, or anti-histamines to those containing anti-inflammatory agents, which reduce basophils and eosinophils present in the mucosal epithelium of the respiratory tract and lymphocytes and which inhibit release of cytokines from lymphocytes; release of mediators from basophils; secretion from glandular cells; vascular permeability; etc. Among such anti-inflammatory agents, steroid compounds exerting great therapeutic effects and less side effects have become of interest in terms of topical therapy, and heretofore, several steroid drugs that can be administered to the respiratory tract through inhalation have been developed.

However, when steroids, which are generally thought to exert a local anti-inflammatory activity, are administered to the respiratory tract, satisfactory site selectivity is not always attained. Steroids which are used at present still have unsatisfactory site selectivity, and safety of these drugs is not fully assured (e.g., grave side effect is induced by long-term administration).

Therefore, there is a demand for development of a steroid for use as a therapeutic agent for inflammatory respiratory tract diseases which exerts an excellent anti-inflammatory effect and which exerts high site selectivity and no systemic effect due to low bioavailability, when administered directly to the nasal cavity or to the respiratory tract via inhalation.

DISCLOSURE OF THE INVENTION

An object of the present invention is to provide a preventive and/or therapeutic agent for inflammatory respiratory tract diseases which exerts excellent anti-allergy and anti-inflammatory effects; exhibits high site selectivity to the respiratory tract; and exerts low systemic side effects.

Under such circumstances, the present inventors have carried out extensive studies on current steroid compounds, and have found that steroid derivatives represented by the following formula (1) exert excellent anti-allergy and anti-inflammatory effects and, when administered directly to the respiratory tract, exhibit high site selectivity and can prevent and/or treat inflammatory respiratory tract diseases without exhibiting substantial systemic side effects. The present invention has been accomplished on the basis of this finding.

Accordingly, the present invention provides a preventive and/or therapeutic agent for inflammatory respiratory tract diseases containing, as an active ingredient, a steroid derivative represented by the following formula (1):

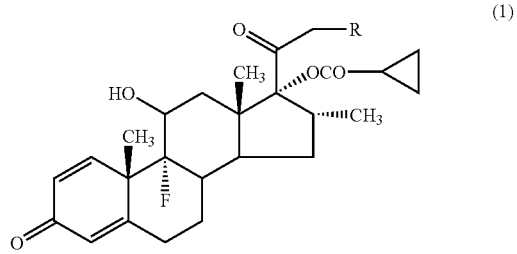

(wherein R represents a hydrogen atom, a halogen atom, a hydroxy group, or —OCOR$^1$ (wherein R$^1$ represents a linear or branched alkyl group which may be substituted by a halogen atom or a cycloalkyl group; a cycloalkyl group; or an aryl group)).

The present invention also provides use of the steroid derivative for producing a preventive and/or therapeutic agent for inflammatory respiratory tract diseases.

The present invention also provides a method for treating an inflammatory respiratory tract disease, characterized by administering the steroid derivative through peroral inhalation or to the nasal cavity.

Figure 1:
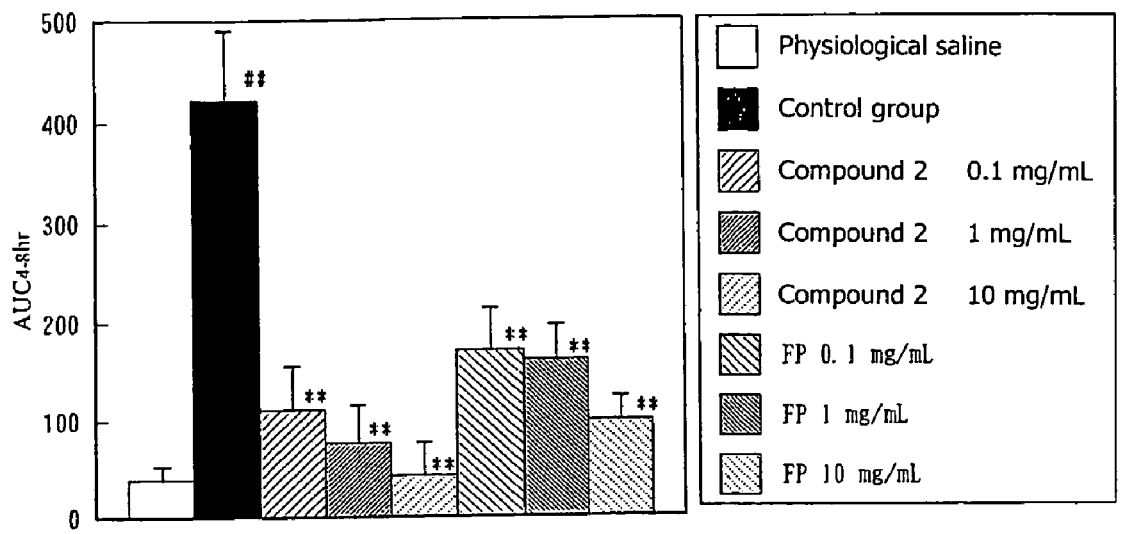
FIG. 1 is a graph showing the areas under curves representing airway resistance during later-onset phase after administration of Compound 2.

(A): Administration of Compound 2 (2%, 4%, or 8%) 24 hours before challenging.

(B): Administration of Compound 2 (8%) 12, 24, and 48 hours before challenging.

BEST MODE FOR CARRYING OUT THE INVENTION

In the preventive and/or therapeutic agent for inflammatory respiratory tract diseases of the present invention, the halogen atom represented by R in formula (1) is preferably fluorine, chlorine, bromine, or iodine. Of these, chlorine and bromine are particularly preferred.

The linear or branched alkyl group represented by R$^1$ is preferably a C1–C23 alkyl group. Of these, a C1–C15 alkyl group is particularly preferred. The halogen atom which may substitute the alkyl group is preferably fluorine, chlorine, bromine, or iodine, with chlorine or bromine being particularly preferred. The cycloalkyl group which may substitute the alkyl group is preferably a C3–C6 cycloalkyl group.

Examples of preferred linear alkyl groups represented by R$^1$ include methyl, ethyl, n-propyl, n-butyl, n-nonyl, n-undecanyl, n-tridecanyl, and n-pentadecanyl. Examples of preferred branched alkyl groups include isopropyl, isobutyl, sec-butyl, t-butyl, isopentyl, neopentyl, t-pentyl, and isohexyl. Examples of the preferred halogenoalkyl group include 3-chloropropyl, 3-bromopropyl, 3-fluoropropyl, 4-chlorobutyl, 4-bromobutyl, 4-fluorobutyl, 5-chloropentyl, 5-bromopentyl, 5-fluoropentyl, 6-chlorohexyl, 6-bromohexyl, and 6-fluorohexyl. Examples of preferred cycloalkylalkyl groups include 2-cyclohexylethyl, 2-cyclopropylethyl, 2-cyclopentylethyl, 3-cyclopropylpropyl, 3-cyclopentylpropyl, 3-cyclohexylpropyl, 4-cyclopropylbutyl, 4-cyclopentylbutyl, 4-cyclohexylbutyl, 5-cyclopropylpentyl, 5-cyclopentylpentyl, 5-cyclohexylpentyl, and 6-cyclopentylhexyl. Examples of preferred cycloalkyl groups include cyclopropyl, cyclobutyl, cyclopentyl, and cyclohexyl. Examples of preferred aryl groups include phenyl, naphthyl, 2-methylphenyl, 4-methylphenyl, 2-ethylphenyl, 4-ethylphenyl, 2-methoxyphenyl, 4-methoxyphenyl, 2-ethoxyphenyl, 4-ethoxyphenyl, 2-aminophenyl, 4-aminophenyl, 4-dimethylaminophenyl, 2-hydroxyphenyl, 4-hydroxyphenyl, 2-nitrophenyl, 4-nitrophenyl, 2-chlorophenyl, 4-chlorophenyl, 2-bromophenyl, 4-bromophenyl, 2-fluorophenyl, 4-fluorophenyl, 2,6-dichlorophenyl, 2,6-dibromophenyl, and biphenyl.

A steroid derivative in which R is, among others, a hydroxy group or —OCOR$^1$ (R$^1$ is a cyclohexyl group) is particularly preferred from the viewpoint of effectiveness.

The steroid derivatives represented by formula (1) are known compounds which exert an excellent anti-inflammatory effect and are useful for treating chronic rheumatoid diseases or similar diseases. Any of the steroid derivatives can be produced through any known method (Japanese Patent Publication (kokoku) No. 7-116215).

The above steroid derivatives are known to exhibit high percutaneous absorption and site selectivity, and thus to be useful as a steroid for external application. However, nothing has ever been known as to whether or not the derivatives can be directly administered to the respiratory tract mucosa. In fact, until the present invention was made, it has never been expected that the steroid derivatives have excellent characteristics; i.e., when administered to the respiratory tract, the derivatives exhibit high site selectivity and no substantial systemic effects.

The target inflammatory respiratory tract diseases of the therapeutic agent of the present invention include upper respiratory tract inflammatory diseases and lower respiratory tract inflammatory diseases as well as laryngeal allergy, chronic obstructive pulmonary diseases, interstitial pneumonia, and similar diseases. Examples of the upper respiratory tract inflammatory diseases include nasal hypersensitivity such as allergic rhinitis or vasomotor (essential) rhinitis and sinusitis, and examples of the lower respiratory tract inflammatory diseases include bronchitis, bronchial asthma, and infantile asthma.

Notably, in the present invention, the term "allergic rhinitis" refers to any allergic response of the nasal mucosa, including pollinosis (seasonal allergic rhinitis) and perennial allergic rhinitis, which are characterized by sneezing, pituita, blockage, itch, eye itch, congestion, or lacrimation.

Bronchial asthma is classified into immediate asthma response, later-onset asthma response, or post later-onset asthma response (allergic asthma), in chronological order, from the viewpoint of the pathological response of the respiratory tract. The preventive and/or therapeutic agent of the present invention can be applied to any of these asthma responses, and are particularly effective to later-onset asthma response, which onsets several hours after exposure of an antigen and whose predominant pathological condition is inflammatory response in the respiratory tract.

The preventive and/or therapeutic agent for inflammatory respiratory tract diseases of the present invention is administered directly to the respiratory tract mucosa, for example, to the nasal cavity or orally administered via inhalation.

A drug preparation for administration to the nasal cavity of the preventive and/or therapeutic agent of the present invention may be prepared in the form of a liquid or powder composition and administered by use of a pressurized dose sprayer, a dry powder sprayer, an instillation container, or a similar device.

A drug preparation for oral inhalation of the preventive and/or therapeutic agent of the present invention may be prepared in the form of a liquid or powder composition and administered by use of a pressurized dose inhaler, a dry powder inhaler, a jet-nebulizer, a supersonic nebulizer, or a similar device.

Such a liquid or powder composition containing the preventive and/or therapeutic agent is produced in the following manner. Compound (1) (active ingredient) is mixed, in accordance with needs, with an excipient, which imparts a shape to the liquid or powder composition, such as a solvent, a base, a diluent, a filler, or an extender; a coadjuvant, which has a function to aid to keep the shape of the liquid or powder composition, such as a dissolution aid, a solubilizer, a buffer, an isotonicity agent, an emulsifier, a surfactant, a stabilizer, a suspending agent, a dispersing agent, a thickener, a lubricant, a binder, an adhesion-resistant agent, or a nebula; and additives, which are added for the purpose of improving properties of the composition upon use, such as a preservative, a bacteriocide, an antiseptic, a sweetening agent, a flavoring agent, an aromatic substance, a coloring agent, and an anti-oxidant. The mixture is processed through a routine method, to thereby prepare a drug preparation for intranasal administration or oral administration via inhalation.

The dose of the active ingredient of the present invention that is effective for prevention and/or therapy varies depending on the route of administration and the age, sex, and severity of conditions of the patient. The daily dose of the active ingredient is typically approximately 50 to 2000 μg, preferably approximately 100 to 800 μg. The dose is typically administered once a day or several times a day in a divided manner. Therefore, drugs are preferably prepared so as to be adapted to the above conditions.

The thus-prepared preventive and/or therapeutic agents for inflammatory respiratory tract diseases according to the present invention exhibit significant inhibitory effects on increase in airway resistance and nasal cavity resistance and substantially no systemic effects, as will be described in Examples described hereinbelow. Specifically, in guinea pig and rat allergic asthma (respiratory tract contraction) models, these agents were administered via inhalation, and also, in a guinea pig allergic rhinitis model, these agents were administered via inhalation or through nasal dropping. Therefore, the preventive and/or therapeutic agents for inflammatory respiratory tract diseases of the present invention are clinically useful, since the agents exert substantially no side effects and are highly safe.

EXAMPLES

Production Example

In accordance with the method described in Japanese Patent Publication (kokoku) No. 7-116215, 9-fluoro-11β,17,21-trihydroxy-16α-methyl-1,4-pregnadiene-3,20-dione 17-cyclopropanecarboxylate (Compound 1) and 9-fluoro-11β,17,21-trihydroxy-16α-methyl-1,4-pregnadiene-3,20-dione 21-cyclohexanecarboxylate 17-cyclopropanecarboxylate (Compound 2) were synthesized.

Specifically, dexamethasone was reacted with a trialkyl ortho cyclopropanecarboxylate in the presence of an acid, to thereby yield an intramolecular ortho ester. Subsequently, the ortho ester was subjected to acid hydrolysis, to thereby yield Compound 1. Further, Compound 1 was reacted with a reactive derivative of cyclohexanecarboxylic acid, whereby Compound 2 was obtained.

Example 1

Effect on Guinea Pig Allergic Asthma Model

A 1% ovalbumin solution was administered to male guinea pigs (8 animals per group) via inhalation for 10 minutes per day for consecutive 8 days. One week after the final sensitization, a 2% ovalbumin solution was administered to each of the guinea pigs via inhalation for 5 minutes (challenging) Both 24 hours and 1 hour before challenging, metyrapon (10 mg/kg) had been intravenously administered to the guinea pig, and, 30 minutes before challenging, pyrilamine (10 mg/kg) had been intraperitoneally administered. Airway resistance (sRaw) of the guinea pig was measured by use of a comprehensive respiratory function analysis system (Pulmos-I, M.I.P.S.). The area under the curve of the sRaw increase rate from 4 to 8 hours after challenging was determined, and the resultant value was employed as an index of delayed type response. Compound 2 of the present invention or fluticazone propionate (FP) suspended in 0.2% HCO-60 physiological saline was administered to the guinea pig via inhalation for 30 minutes both 24 hours and 1 hour before challenging. The results are shown in FIG. 1.

As is apparent from FIG. 1, as compared with FP, the preventive and/or therapeutic agent of the present invention exhibits an enhanced inhibitory effect on later-onset asthma response (LAR), which is a type of guinea pig allergic asthma response.

Example 2

Effect on Guinea Pig Allergic Rhinitis Model

Figure 2:
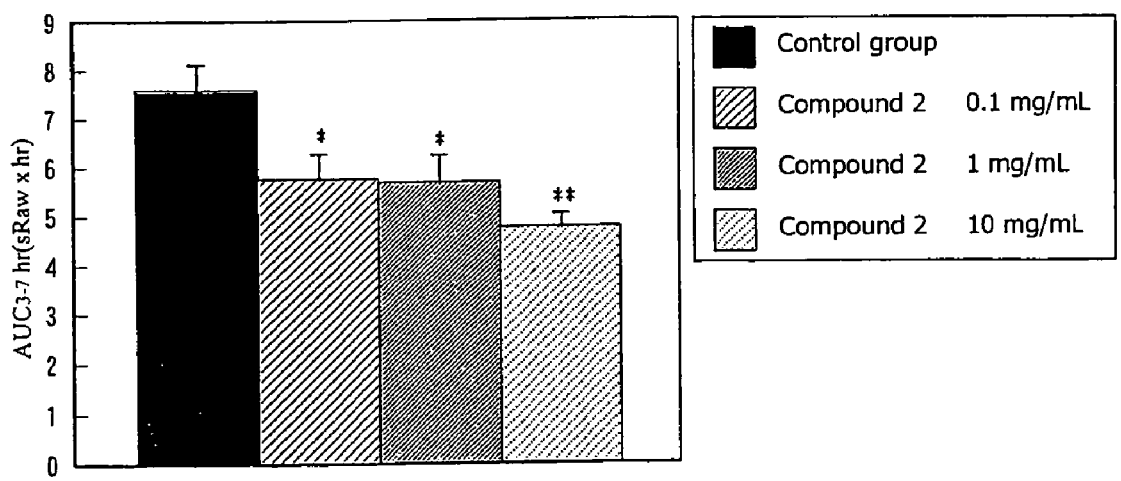
FIG. 2 is a graph showing the areas under curves representing nasal cavity resistance during later-onset phase after administration of Compound 2.

A 20 μg/mL ovalbumin solution was mixed with the equivalent amount of a 20 mg/mL aluminum hydroxide gel solution, and the mixture was intraperitoneally administered to male guinea pigs (9 animals per group) in a volume of 1 mL/animal. One week after the administration, the same procedure was repeated. From one week after the final sensitization, induction of rhinitis was repeated once a week. Two days, one day, and one hour before the fifth induction (three times in total), Compound 2 of the present invention suspended in 0.2% HCO-60 physiological saline was administered to each nasal cavity of the guinea pigs in a volume of 20 μL (total 40 μL per animal). Rhinitis was induced by administering 0.1 mg/mL ovalbumin solution to each nasal cavity of the guinea pigs in a volume of 20 μL (total 40 μL per animal). Nasal cavity resistance (sRaw) was measured by use of a comprehensive respiratory function analysis system (Pulmos-I, M.I.P.S.). The area under the curve of sRaw increase rate from 3 to 7 hours after challenging was determined, and the resultant value was employed as an index of later-onset asthma response. The results are shown in FIG. 2.

As is apparent from FIG. 2, the preventive and/or therapeutic agent of the present invention was found to exhibit an inhibitory effect on later-onset asthma response (LAR), which is a type of guinea pig allergic asthma response.

Example 3

Effect on Rat Allergic Asthma Model

An equivolume mixture of a 20 μg/mL ovalbumin solution and a 5 mg/mL aluminum hydroxide gel solution was intraperioneally administered to rats (7 animals per group) at a volume of 1 mL per animal for sensitization. For additional sensitization, one day and two days after the administration, the same procedure was repeated. Thirteen days after the sensitization, an antigen (a 2% ovalbumin solution) was administered to each rat via inhalation for 25 minutes (challenging). Twenty-four hours after the challenging, the respiratory tract was washed with physiological saline, and the number of inflammatory cells (eosinophils) floating in the wash saline was counted for use as an index of asthma response.

Figure 3:
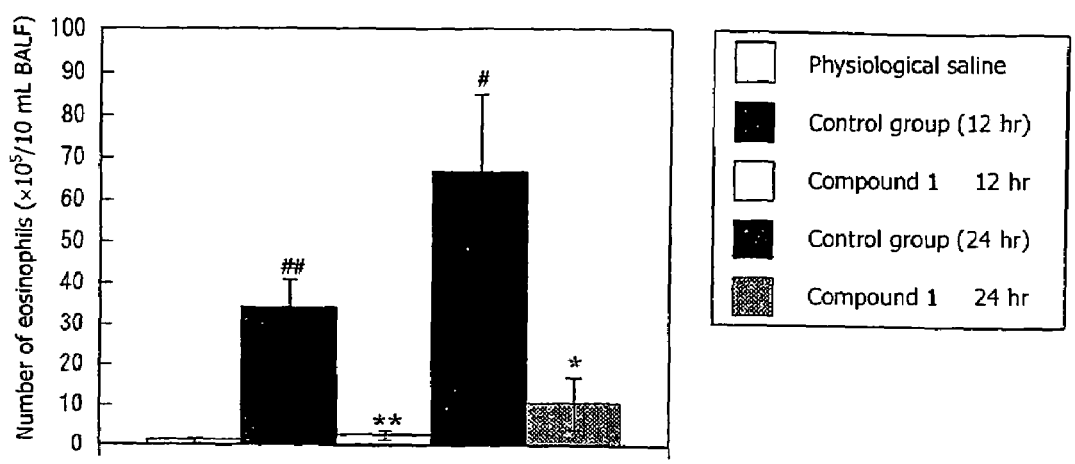
FIG. 3 is a graph showing the number of eosinophils after administration of Compound 1.

(1) Compound 1 of the present invention was diluted with lactose (8%). Twenty-four hours and 12 hours before challenging, the powdered drug preparation thereof was intratracheally administered in an amount of 10 mg per rat. The results are shown in FIG. 3.

Figure 4:
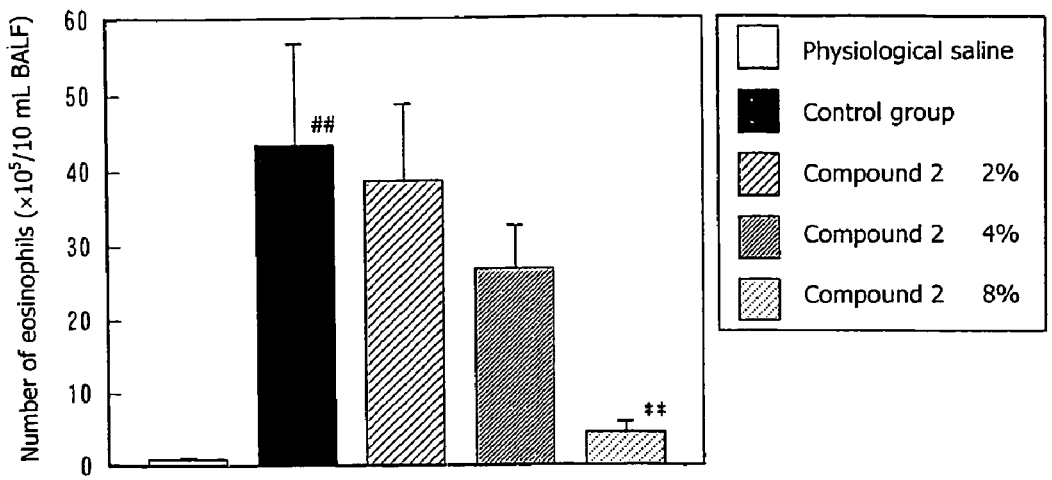
FIGS. 4(A) and 4(B) are graphs showing the number of eosinocytes after administration of Compound 2.
Figure 4:
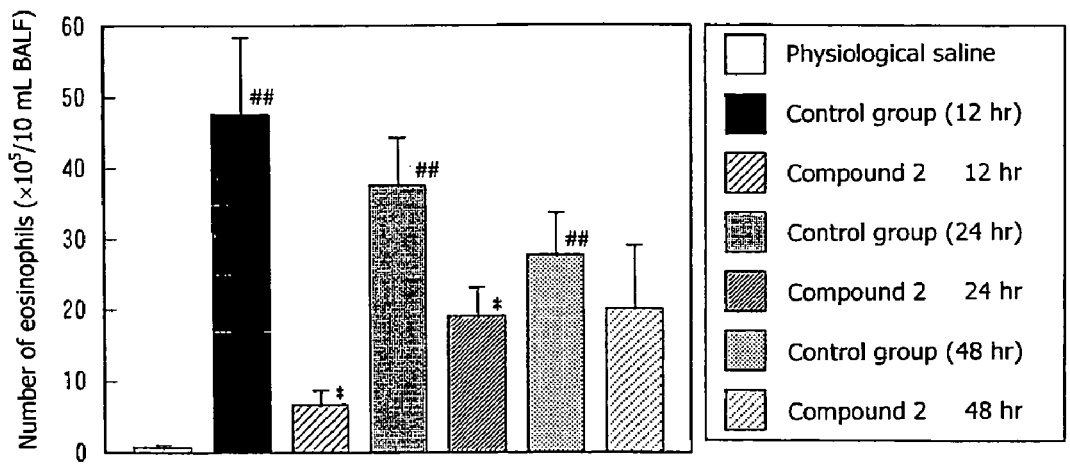

(2) 1) Compound 2 of the present invention was diluted with lactose (2%, 4%, and 8%). Twenty-four hours before challenging, each of the powdered drug preparations thereof was intratracheally administered in an amount of 10 mg per rat. The results are shown in FIG. 4(A).

2) Forty-eight, twenty-four, and twelve hours before challenging, the powdered drug preparation containing 8% Compound 2 of the present invention was intratracheally administered in an amount of 10 mg per rat. The results are shown in FIG. 4(B).

The test results indicate that the anti-asthma effect of the preventive and/or therapeutic agents of the present invention continues for 24 hours or longer when administered in a powder form.

Example 4

Single Dose Toxicity Study

Compound 1 or 2 of the present invention was administered to rats only once, and the lethal dose thereof was determined. The results are shown in Table 1. Compounds 1 and 2 of the present invention were confirmed to exhibit low toxicity.

TABLE 1

| Animal species (sex) | Route of administration | Lethal dose (In general) |
|---|---|---|
| Rat (male, female) | Oral | 2,000 mg/kg or more |
| Rat (male, female) | Subcutaneous | 2,000 mg/kg or more |

Example 5

Preparation Examples (1) Inhalant

Powder for inhalation was prepared according to the following formulation through a routine process.

| | |
|---|---|
| Compound 1 or 2 | 0.8 mg |
| Lactose | 19.2 mg |
| Total | 20.0 mg |

(2) Nasal Drop

A solution for nasal drop were prepared according to the following formulation through a routine process.

| | |
|---|---|
| Compound 1 or 2 | 0.01% w/w |
| Sodium carboxymethylcellulose | 1.0% w/w |
| Sodium chloride | 0.9% w/w |
| Purified water is used to balance (total 100%). | |

INDUSTRIAL APPLICABILITY

The steroid derivative of the present invention represented by formula (1) can continuously suppress respiratory tract inflammation and respiratory tract hyperreaction and shows high site selectivity and little systemic effect when administered directly to the respiratory tract. Therefore, the steroid derivative of the present invention is remarkably useful in clinical medicine as a highly safe preventive and/or therapeutic agent for inflammatory respiratory tract diseases which can be administered for a long period of time.

What is claimed is:

1. A method for treating an inflammatory respiratory tract disease, comprising administering a steroid derivative through peroral inhalation or intranasally, wherein the steriod derivative is represented by the following formula (1):

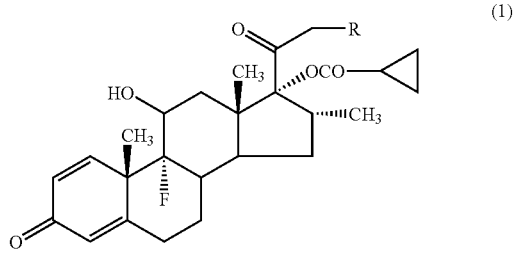

(wherein R represents a hydrogen atom, a halogen atom, a hydroxy group, or —OCOR$^1$ (wherein R$^1$ represents a linear or branched alkyl group which may be substituted by a halogen atom or a cycloalkyl group; a cycloalkyl group; or an aryl group)).

2. The method as described in claim 1, wherein the steroid derivative is 9-fluoro-11β,17,21-trihydroxy-16α-methyl-1,4-pregnadiene-3,20-dione 17-cyclopropanecarboxylate or 9-fluoro-11β,17,21-trihydroxy-16α-methyl-1,4-pregnadiene-3,20-dione 21-cyclohexanecarboxylate 17-cyclopropanecarboxylate.

3. The method as described in claim 1, wherein the inflammatory respiratory tract diseases is selected from the group consisting bronchial asthma, nasal hypersensitivity, laryngeal allergy, and sinusitis.

4. The method as described in claim 2, wherein the inflammatory respiratory tract disease is selected from the group consisting of bronchial asthma, nasal hypersensitivity, laryngeal allergy, and sinusitis.

5. The method as described in claim 1, wherein the steroid derivative is administered as a powder.

6. The method as described in claim 1, wherein the steroid derivative is administered as a liquid.

* * * * *

UNITED STATES PATENT AND TRADEMARK OFFICE
CERTIFICATE OF CORRECTION

PATENT NO.       : 7,214,672 B2                                                Page 1 of 1
APPLICATION NO.  : 10/451061
DATED            : May 8, 2007
INVENTOR(S)      : Komoto et al.

It is certified that error appears in the above-identified patent and that said Letters Patent is hereby corrected as shown below:

On the title page, Item (75), the inventors information is incorrect. Item (75) should read:

-- (75) Inventors: Teruo Komoto, Chiba (JP); Hiroyuki Mizuno, Inba-gun (JP); Yoshinori Takahashi, Inba-gun (JP); Koichi Takahashi, Inba-gun (JP); Susumu Sato, Narita (JP) --

Signed and Sealed this

Twenty-sixth Day of June, 2007

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,214,672 B2 | Page 1 of 1 |
| APPLICATION NO. | : 10/451061 | |
| DATED | : May 8, 2007 | |
| INVENTOR(S) | : Teruo Komoto et al. | |

It is certified that error appears in the above-identified patent and that said Letters Patent is hereby corrected as shown below:

On the title page, Item 54 and col 1, please correct the title of the patent to read:

--PREVENTION/THERAPEUTIC AGENT FOR INFLAMMATORY RESPIRATORY TRACT DISEASES--.

Column 8, line 29, "consisting bronchial" should read --consisting of bronchial--.

Signed and Sealed this

Twenty-second Day of July, 2008

JON W. DUDAS
*Director of the United States Patent and Trademark Office*